United States Patent [19]

Freund et al.

[11] Patent Number: 4,742,825
[45] Date of Patent: May 10, 1988

[54] ADJUSTABLE COMPRESS APPARATUS

[75] Inventors: Robert F. Freund, Centerville; Lawrence J. Richards, Dayton; Stanley L. Flowers, West Milton, all of Ohio

[73] Assignee: Freund Medical Products, Inc., Dayton, Ohio

[21] Appl. No.: 903,775

[22] Filed: Sep. 5, 1986

[51] Int. Cl.⁴ ............................................. A61B 17/12
[52] U.S. Cl. .................................. 128/325; 128/346; 248/124
[58] Field of Search ............... 128/325, 327, 346, 361, 128/303 R, 108; 248/298, 295.1, 125, 124

[56] References Cited

U.S. PATENT DOCUMENTS

| | | |
|---|---|---|
| 37,156 | 12/1862 | Dunton . |
| 1,281,653 | 10/1918 | Plummer ........................... 128/327 |
| 1,561,116 | 11/1925 | Silliman . |
| 2,712,314 | 7/1955 | Kohl . |
| 3,625,219 | 12/1971 | Abrams . |
| 3,779,249 | 12/1973 | Semler . |
| 3,802,439 | 4/1974 | Baumgarten . |
| 3,884,240 | 5/1975 | Gilman . |
| 4,106,508 | 8/1978 | Berlin . |
| 4,233,980 | 11/1980 | McRae ............................... 128/325 |
| 4,314,568 | 2/1982 | Loving . |
| 4,390,018 | 6/1983 | Zukowski . |
| 4,509,528 | 4/1985 | Sahota ................................ 128/691 |
| 4,557,262 | 12/1985 | Snow . |
| 4,572,182 | 2/1986 | Royse . |
| 4,572,185 | 2/1986 | Royse ................................. 128/325 |

FOREIGN PATENT DOCUMENTS 7903156 8/1980 France .

*Primary Examiner*—Dalton L. Truluck
*Assistant Examiner*—F. Wilkens
*Attorney, Agent, or Firm*—Killworth, Gottman, Hagan & Schaeff

[57] ABSTRACT

An adjustable compress apparatus for applying adjustable pressure to a patient in the area of a puncture site on a patient includes an adjustable stand, a pressure adjustment mechanism and a pressure pad. The adjustable stand has a support frame and a patient size adjustment mechanism movably mounted thereon for adjusting the size and the orientation of the stand to accommodate patients of various sizes. The pressure adjustment mechanism is mounted to the outer end of the patient size adjustment mechanism and, in turn, supports the pressure pad in pressure contact with the patient. By adjustment of the latter mechanism, the pressure applied to the puncture site by the pressure pad can be gradually and finely adjusted. The pressure pad is attached to the pressure adjustment mechanism by a ball-and-socket connection which permits a range of movement of the pad relative to the patient for self-adjustment of the pad into conformity with the contour of the patient's body.

19 Claims, 3 Drawing Sheets

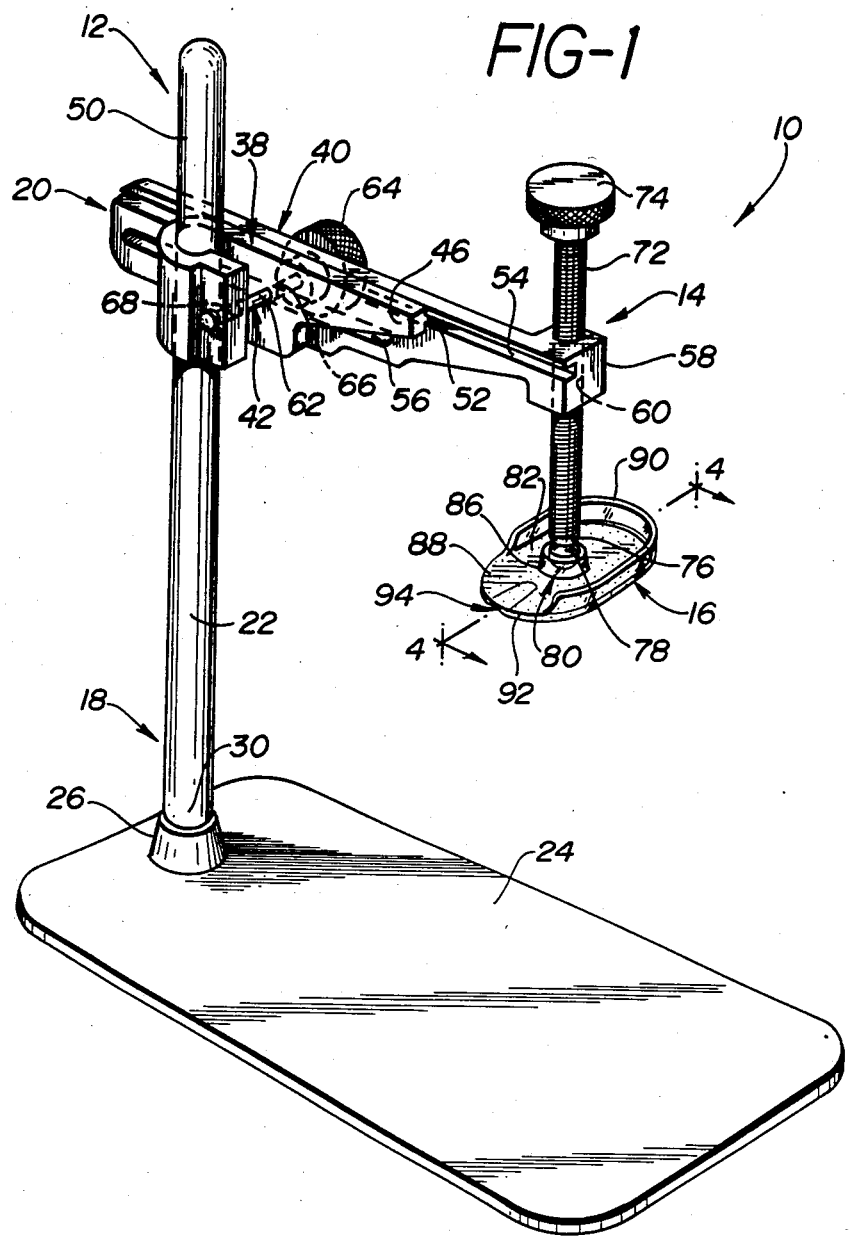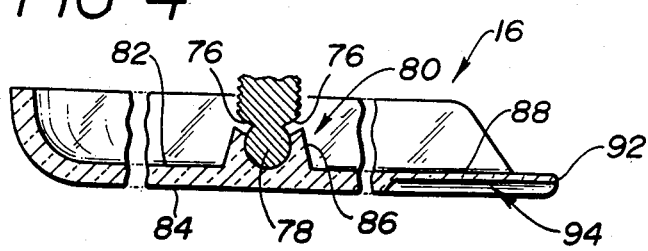

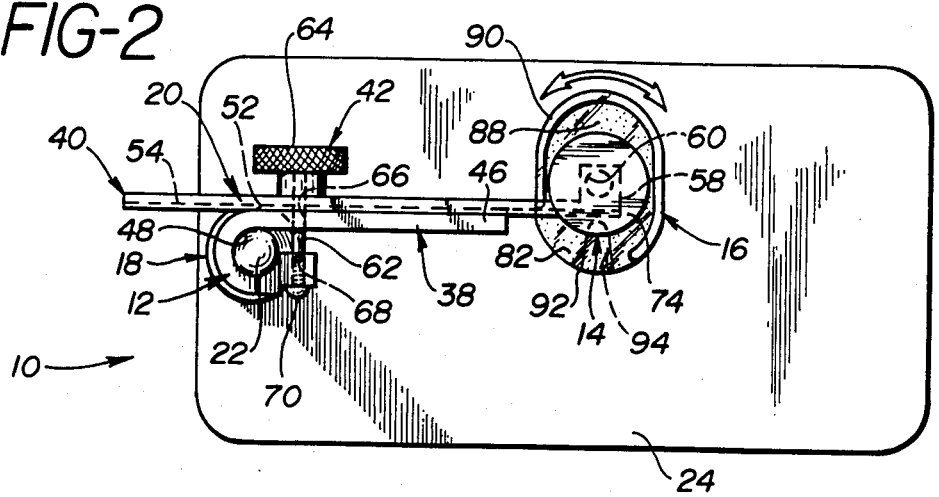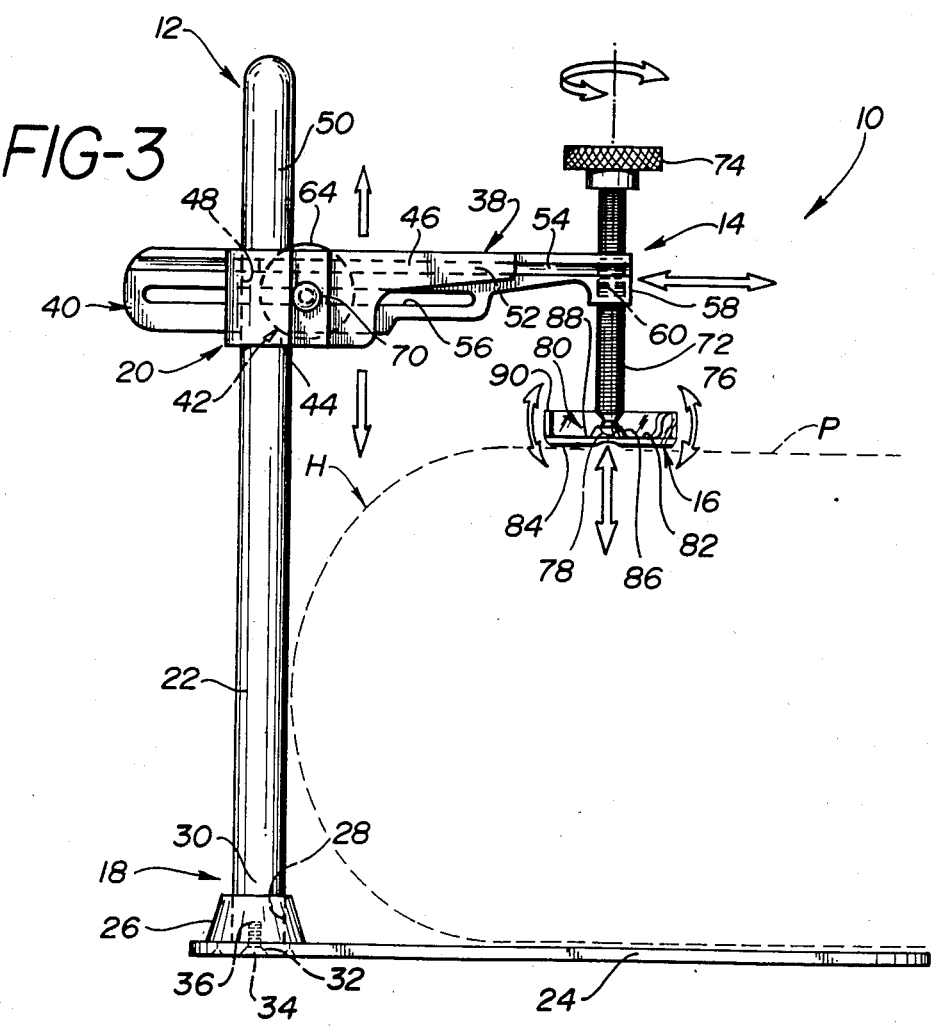

ADJUSTABLE COMPRESS APPARATUS

BACKGROUND OF THE INVENTION

The present invention generally relates to medical instruments used to prevent bleeding and, more particularly, to a compress apparatus which employs multiple mechanisms to adjust the apparatus for use with patients of various sizes and to permit controlled application and release of the pressure applied to a puncture site on the patient.

Medical procedures involving the puncture of a blood vessel for purposes of entry of a catheter or a needle are commonly performed. One such procedure is a cardiac catheterization in which the femoral artery in a patient's groin area is punctured to allow passage of a long, fine catheter through the artery and into the chambers of the heart. The cardiac catheterization procedure aids in diagnosis of various heart disorders and anomalies.

Following withdrawal of the catheter, pressure must be applied to the groin area at the location of the puncture in the artery to allow coagulation to take place to prevent bleeding. Several approaches to apply the necessary pressure have been followed. One approach is for a physician or nurse to manually apply pressure to the site of the puncture for an extended period of time. However, this is time consuming and restricts the freedom of such medical personnel to render other urgent medical care.

Another approach is to use a mechanical device to apply the pressure. A device designed for this purpose is disclosed in U.S. Pat. No. 3,779,249 which issued to Semler. This device, called an artery clamp, includes an upright tubular support member mounted on a flat base, and an arm structure mounted from the support member in cantilevered fashion overlying the base. The arm structure is mounted for vertical slidable movement along the upper end of the support member. Detachably mounted at the outer end of the arm structure is a relatively inflexible. disk-shaped pressure pad formed from a transparent plastic material.

Before removing the catheter from the patient, a physician or nurse places the base of the clamp device under the patient's thigh and slidably positions the arm structure so that the pressure pad is directly over the puncture site. As the catheter is withdrawn, the arm structure is manually moved down toward the base, causing the pad to compress the artery and prevent bleeding. The resulting upward pressure on the pad causes slight upward pivoting of the arm structure relative the upright support member which locks the arm structure in position on the support member. After a period of time sufficient for coagulation, the arm structure is unlocked by manually operating a release lever mounted thereon. If bleeding recurs, the user may re-compress the blood vessel by again pressing down on the arm structure.

Later U.S. Pat. No. 4,572,182 to Royse proposes that the pressure pad used with the artery clamp of the Semler patent have a V-shaped notch formed through it. This permits the pad to apply pressure to the puncture site prior to complete removal of the catheter. The V-shaped notch receives the catheter as the latter is being withdrawn from the puncture site.

The above described artery clamp of the Semler patent is advantageous in that it relieves a physician or nurse from the restrictive task of manually applying pressure to the puncture site. However, it embodies several limitations which make it less that an optimum solution to the problem of preventing bleeding in a reliable manner.

One limitation of the Semler clamp device is that its arm structure is of fixed length. As a consequence, when used with patients of slender or small size, the device must be positioned substantially outwardly from the patient's side in order to have the pressure pad properly located with respect to the puncture site. This is undesirable from the standpoint of stability of the device during use. Another limitation is that there is no easy way to adjust the amount of pressure being applied to the patient once the arm structure has been moved down and locked into position, especially in view of the fact that locking of the arm structure is dependent upon an upward reaction force being applied to it by the patient's body. Although the arm structure can be locked at an infinite number of different positions along the support member, there is no means to accurately adjust the arm structure to any one selected position. Instead, trial and error is involved to find the approximate position required to apply the proper amount of pressure.

Yet another limitation is that the procedure for removal of the pressure pad is somewhat jerky. When the pressure pad is abruptly moved away from the patient, the blood clot which seals the puncture wound may tear, allowing bleeding to resume. Still another limitation is that the conical socket used to mount the pressure pad to the outer end of the arm structure does not allow significant conformance of the attitude of the pad to the contour of the patient's body at the puncture site. As a result, a situation is likely to arise where an uneven distribution of pressure is applied to the site. Yet another limitation is that the flat bottom surface of this pad is bordered by a relative sharp edge which may tend to dig uncomfortably into the patient's skin if the upper torso of the patient is raised slightly. Often it is desirable, however, to elevate the upper torso to facilitate normal breathing patterns and enhance patient comfort.

Consequently, in view of the above-cited limitations, as well as others embodied by the construction of the Semler clamp device, it is readily apparent that a need exists for a device which addresses the limitations of the prior art and provides improved operation and patient comfort.

SUMMARY OF THE INVENTION

The present invention provides an adjustable compress apparatus designed to satisfy the aforementioned needs. The adjustable compress apparatus of the present invention embodies design features which avoid all of the above-described limitations of the prior art by providing a high degree of adjustability in positioning the device, in selecting the proper pressure to apply and finely adjusting the pressure, and in distributing evenly the applied pressure. The advantages of the compress apparatus of the present invention are primarily its greater adjustability in all of these aforementioned. respects, and its improved ease of operation over the prior art device.

Principally, the adjustable compress apparatus of the present invention is particularly useful in applying adjustable pressure to a puncture site on a patient of any size. In its basic components, the apparatus includes an adjustable stand, a pressure pad, and a pressure adjustment mechanism.

More particularly, the adjustable stand includes a support frame and a patient size adjustment mechanism. The support frame extends in upright relation and is positionable closely adjacent to a patient when the patient is reclining on a support surface. The patient size adjustment mechanism is mounted to the support frame for movement therealong to adjust the mechanism to an appropriate height above the support surface. The mechanism is also movable generally transversely with respect to the support frame to adjust the mechanism to span a range of distances across the patient from the puncture site thereon to the support frame. Such adjustment of the mechanism allows placement of the support frame closely adjacent to the patient, with a portion of the mechanism located in a desired relation overlying the puncture site on the patient.

Still further, the pressure adjustment mechanism is mounted to that portion of the patient size adjustment mechanism overlying the puncture site for movement toward and away from the patient reclining on the support surface. The pressure adjustment mechanism has a lower end disposed adjacent to and overlying the puncture site which supports the pressure pad at the puncture site and in pressure contact therewith. The amount of pressure applied to the puncture site by the pressure pad is adjustable upon movement of the pressure adjustment mechanism toward and away from the patient. The lower end of the pressure adjustment mechanism supports the pressure pad via a releasable ball-and-socket connection permitting pivotal movement of the pad relative to the patient for self-adjustment of the pad into conformity with the contour of the patient's body in the area of the puncture site.

Accordingly, it is an object of the present invention to provide a simple compress apparatus with an adjustable stand having a patient size adjustment mechanism which can be adjusted to adapt the stand to patients of varying sizes; to provide a compress apparatus with a pressure adjustment mechanism which can be adjusted to select the proper pressure to apply to a puncture site on a patient of any size, and which can be used to finely and gradually adjust the pressure being applied to the puncture site; and to provide an omni-directional joint connecting a pressure pad to the pressure adjustment mechanism which permits even or uniform distribution of the adjustable pressure applied by the pressure pad to the patient's body in the area of the puncture site; and to provide a means of applying pressure to the puncture site in a controlled manner without causing the pressure pad to rotate.

BRIEF DESCRIPTION OF THE DRAWINGS

FIG. 1 is a perspective view of the adjustable compress apparatus of the present invention;

FIG. 2 is a top plan view of the compress apparatus of FIG. 1;

FIG. 3 is a side elevational view of the compress apparatus of FIG. 1:

FIG. 4 is a vertical sectional view of a first embodiment of the pressure pad and the ball-and-socket connection between the pressure adjustment mechanism and the pressure pad;

DETAILED DESCRIPTION OF THE PREFERRED EMBODIMENT

Figure 5:
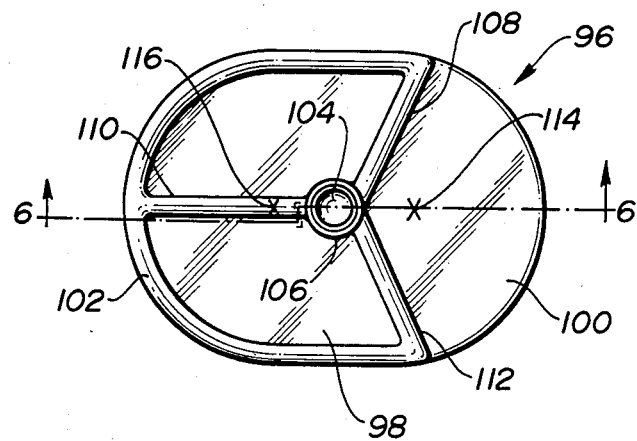
FIG. 5 is a top plan view of a second embodiment of the pressure pad.

Reference is made to FIGS. 1 to 3 of the drawings which illustrate an adjustable compress apparatus, generally designated 10, comprising the preferred embodiment of the present invention. Although not so limited, the compress apparatus 10 is principally useful in applying adjustable pressure to a puncture site in the groin region of a patient's body, the position of the patient's body being represented generally in phantom outline form in FIG. 3. In its basic components, the adjustable compress apparatus 10 includes an adjustable stand 12, a pressure adjustment mechanism 14 and a pressure pad 16. In an exemplary embodiment of the compress apparatus, the parts of the adjustable stand 12 are fabricated from aluminum, the pressure adjustment mechanism 14 from stainless steel, and the pressure pad 16 from transparent polyethylene. It will be apparent, however, that other materials, such as for example plastic, may be utilized.

More particularly, the adjustable stand 12 includes a support frame 18 and a patient size adjustment mechanism 20. The support frame 18 has a support post 22, preferably fabricated from a rigid material, and a flat base plate 24 with a support block 26 fixed on the upper side of the plate 24 at one end thereof. The support block 26 has a central recess 28 diametrically sized to snugly receive an end 30 of the support post 22, mounting the post in upright extending relation on the base plate 24. The support block 26 also has a hole 32 through its bottom which communicates with the central recess 28 of the block to receive a screw 34 which is threaded into an internally threaded hole 36 tapped in the lower end of the support post 22. The flat base plate 24 is adapted to be inserted under the patient and rest on the surface which supports the patient. If desired, the support block 26 may be eliminated and a hinge connection arrangement substituted to produce a folding device.

The patient size adjustment mechanism 20 of the stand 12 includes a clamp member 38, an arm member 40 and a releasable locking member 42. The clamp member 38, with an overall J-shaped configuration, has a curved mounting portion 44 and a straight guiding portion 46. The curved mounting portion 44 defines a generally cylindrical passage 48. The upper end portion 50 of the upright support post 22 extends through the clamp member passage 48 in mounting the clamp member 38 thereon above the base plate 24 for slidable movement generally vertically along the support post toward and away from the base plate. The patient size adjustment mechanism 20 may also be pivoted around the support post 22. When the clamp member 38 is mounted on the support post 22, its straight guiding portion 46 extends generally horizontally in transverse relation to the post. Also, the straight guiding portion 46 of the clamp member 38 has a linear guide rail 52 formed thereon which protrudes outwardly from the side of the clamp member 38 opposite the support post 22. The guide rail 52 extends longitudinally along the straight guiding portion 46 of the clamp member 38 and generally parallel to the base plate 24.

The arm member 40 of the patient size adjustment mechanism 20 is longer than the clamp member 38 and has a longitudinal groove 54 defined therein of a cross-sectional size adapted to receive the guide rail 52 of the clamp member 38. The arm member 40 is thereby mounted on the clamp member 38 for slidable movement generally horizontally therealong in transverse relation to the support post 22 and generally parallel relation to the base plate 24. It should be understood that the locations of rail 52 and groove 54 could be reversed, that is, the rail formed on the arm member 40 and the groove on the clamp member 38. The arm member 40 also has a slot 56 defined therein spaced below and extending generally parallel to the groove 54 and an outer end in the form of an enlarged square-shaped block 58 which overlies and may be spaced above the base plate 24 at all possible positions of the arm member 40 along the clamp member 38. The block 58 has an internally threaded opening 60 formed vertically through it.

The releasable locking member 42 of the patient size adjustment mechanism 20 is used to fasten the clamp member 38 at any selected vertical position along the support post 22 and any pivotally adjusted position around the support post and, at the same time, to fasten the arm member 40 at any selected horizontal position along the clamp member 38. Thus, the clamp and arm members 38, 40, and thereby the size of the adjustable stand 12, can be adjusted for locating the block 58 on the outer end of the arm member 40 above and in a desired positional relation with a puncture site on a patient P (FIG. 3) positioned between the arm member 40 and base plate 24, and with the patient's hip H alongside the support post 22 of the stand.

Specifically, the releasable locking member 42 takes the form of an elongated threaded stem 62 having a knob 64 attached on one end. The stem 62 extends through the slot 56 in the arm member 40 and a clearance hole 66 in the straight portion 46 of the clamp member 38, and at its opposite end is threaded through an internally threaded hole 68 tapped in the outer end of the curved portion 44 of the clamp member 38 in alignment with the clearance hole 66. A screw retainer 70 is attached to the opposite end of the threaded stem 62 prevents it from being completely unscrewed from the hole 68. The clamp member 38 is clamped to the support post 22 and the arm member 40 is secured to the clamp member 38 by screwing the stem 62 into the hole 68 until the knob 64 is tightened down against the outer surface of the arm member. Then, by loosening the knob 64, the position of the arm member 40 can be horizontally slidably adjusted along the clamp member 38. At the same time, the position of the clamp member 38 can be vertically slidably adjusted along the support post 22 and adjusted in position about the periphery of the support post.

The pressure adjustment mechanism 14 of the compress apparatus 10 includes an elongated member in the form of a threaded shaft 72 threadably mounted through the opening 60 in the block 58 on the outer end of the arm member 40 of the patient size adjustment mechanism 20. The threaded shaft 72 has a knob 74 attached on its upper end and an inwardly-tapered section 76 defined on its lower end which, in turn, is integrally connected with a spherical ball 78, being part of a ball-and-socket joint, generally designated 80. By turning the knob 74 one direction or the opposite, the shaft 72 can be vertically moved relative to the arm member 40 toward or away from the base plate 24, and thus toward or away from the puncture site in the groin area of the patient P positioned between base plate 24 and the arm member 40. In such manner, the pressure pad 16 mounted to the lower end of the threaded shaft 72, as described below, can be placed in pressure contact with the patient in the area of the puncture site.

Finally, as seen best in FIG. 4, the pressure pad 16 of the compress apparatus 10 includes a generally flat disc-shaped portion 82. It will be appreciated that the term disc-shaped is intended to include various shapes having carved peripheries, such as circular, oval, and eliptical shapes, and the like. Portion 82 may be textured on its lower side 84 to engage securely the patient's skin so that the pad 16 does not rotate when the threaded shaft 72 is turned to adjust the pressure applied by the pad. A socket 86, being part of the ball-and-socket joint 80, is integrally attached to the pad portion 82 at a central location on its upper opposite side 88. The socket 86 on the pressure pad 16 releasably mates with the ball 78 on the threaded shaft 72 for generally pivotal movement of the pad 16 relative to the threaded shaft 72, the range of such movement being limited by the tapered section 76 on the lower end of the shaft.

The pressure pad 16 also has a heel portion 90 formed about and along a portion of the peripheral edge 92 of the disc-shaped portion 82 of the pad; however, the heel portion is absent from the portion of peripheral edge which generally faces the feet of the patient. The heel portion 90 which projects upwardly from the disc-shaped portion 82 extends generally toward the patient's head and is intended to prevent the edge of the pad from cutting uncomfortably into the patient's skin, should the patient's upper torso be raised slightly toward a sitting position.

Finally, the disc-shaped portion 82 of the pad 16 has a groove 94 defined in the lower side 84 thereof. The groove 94 does not extend upwardly through to the upper surface 88 of the pad. The groove 94 at its inner end is spaced from the center of the pad 16 and extends therefrom to the peripheral edge portion thereof without the heel portion 90 thereon. The groove 94 divergently tapers from the center to the peripheral portion of the pad so that it is widest at the peripheral portion. The presence of the groove 94 allows a catheter to be removed with the pad 16 in place and provides a means of locating the pad properly with respect to the puncture site. Also, due to the shallowness of the groove, the pad applies pressure to the patient's skin in the region of the groove.

In setting up the apparatus, the threaded shaft 72 is initially rotated so as to raise the pressure pad 16 as high as possible with respect to the arm member 40. Then, the base plate 24 is moved under the patient's buttocks to position the support post 22 directly against the side of the patient. Following that, the clamp member 38 and arm member 40 are swiveled and adjusted in height above the base plate 24 and in length from the support post 22 such that the pressure pad 16 is held directly over the puncture site on the patient. Before the knob 64 on the threaded stem 62 is tightened down, the clamp member 38 and arm member 40 with the shaft 72 thereon are lowered until the pad 16 is in contact with the patient at the site of the puncture. The knob 64 is then tightened to lock all of these components in fixed position. At this time the adjustment of the stand 12 to fit the size of the patient has been completed.

Next, the knob 74 at the top of the shaft 72 is rotated to press the pad 16 downward against the patient's skin and the catheter is removed from the patient. The present invention then supplies and maintains sufficient force to preclude seepage of blood while the puncture wound clots. This may take approximately half an hour. Using the knob 74 allows for a carefully adjusted pressure to be applied to the puncture site by the pad 16. Since the pad 12 is made out of generally clear plastic material, any bleeding from the puncture site can easily be observed. Initially after withdrawal of the catheter, sufficient force is applied to the puncture site to preclude bleeding. The force is gradually reduced over the following half hour to one hour period by rotating the knob 74. If the amount of reduction in pressure causes a renewal of bleeding, the knob 74 can quickly be tightened down to a pressure level sufficient to prevent this from occurring.

Unlike with the prior art devices, fine adjustment in the level of force or pressure applied to the puncture site can be easily made with the present invention. It will be appreciated that the ability to make such a fine adjustment of the pressure level during application of the pad 16 and release of the pad 16 is important. Too great a force applied to the patient's skin may result in the blood vessel (i.e., femural artery) being blocked and an undesirable termination in the supply of blood to the patient's leg. On the other hand, insufficient pressure may produce seeping through the wound site, creating a hematoma.

Having thus described the adjustable compress apparatus of the present invention in detail and by reference to a preferred embodiment thereof, it will be apparent that modifications and variations are possible without departing from the scope of the invention defined in the appended claims.

Figure 6:
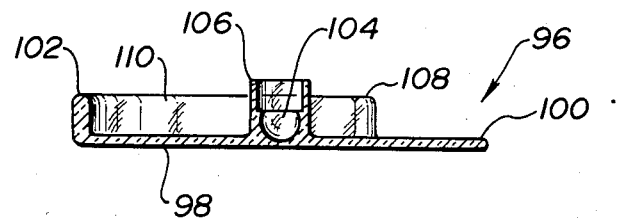
FIG. 6 is a sectional view of the second embodiment of the pressure pad taken generally along line 6—6 in FIG. 5.

FIGS. 5 and 6 illustrate a second embodiment of the pressure pad of the present invention. Pad 96 may preferably be formed of a polyolefin, such as polyethylene. Pad 96 includes a generally flat disc-shaped portion 98, which is sufficiently thin to be at least partially transparent such that any bleeding beneath the pad is readily apparent. Due to the thickness of portion 98, the portion 98 is also relatively flexible in the area indicated at 100. This is desirable in that the end of the pad adjacent area 100 may be flexed upward slightly as pressure is applied to a puncture site and a catheter is simultaneously removed.

The pad 96 also includes a heel portion 102 and a socket 104, part of a ball and socket joint, which are similar to corresponding elements of the first embodiment of the pressure pad discussed above with respect to FIG. 4. It should be noted that socket 104 includes a collar 106 of somewhat greater diameter. The pad 96 is intended to be mounted on a ball at the end of a threaded shaft having a diameter generally equal to that of the ball. As a consequence, upon extreme tilting of the pad 96, the upper edge of collar 106 contacts the side of the shaft. It will be appreciated that the forces necessary to distort the shape of the socket 104 and cause the socket and ball to become disconnected must be greater than would be the case without collar 106.

The pad 96 further includes a plurality of ribs 108, 110, and 112 which extend radially outward from socket 104 to the heel portion 102. Ribs 108, 110, and 112 reinforce the area surrounded by the heel portion 102 and render it substantially stiffer than area 100.

It will be understood that a catheter enters the skin through a puncture site and descends downward to puncture the selected artery at an angle such that the artery puncture site is not directly below the skin puncture site. In use, pad 96 is positioned above the skin puncture site indicated by the "X" at 114. The flexible area 100 will permit some pressure to be applied as the catheter is withdrawn. The ribs 108, 110, and 112 insure that substantial pressure is applied to the artery puncture site, indicated by the "X" at 116.

What is claimed is:

1. Adjustable compress apparatus for use in applying adjustable pressure to a puncture site on a patient, comprising:
   an adjustable stand including
      a support frame extending in upright relation and disposable closely adjacent to a patient when reclining on a support surface, said support frame including a base plate and a support post extending upright therefrom;
      a patient size adjustment mechanism mounted to said support frame for movement along said support frame to adjust said mechanism to a height greater than that of a puncture site on the patient above the support surface and for movement generally transverse to said support frame to adjust said mechanism to span a range of distances across the patient from the puncture site thereon to said support frame when disposed closely adjacent to the patient, so as to locate a portion of said mechanism in a desired relation overlying the puncture site on the patient, said mechanism including
         a clamp member mounted on said support post above said base plate for slidable movement generally vertically along said support post toward and away from said base plate;
         an arm member mounted on said clamp member for slidable movement generally horizontally therealong, in transverse relation to said support post and generally parallel relation to said base plate, said arm member having an outer end defining said portion of said patient size adjustment mechanism overlying said base plate; and
         a releasable locking member for fastening said clamp member at any selected vertical position along said support post and said arm member at any selected horizontal position along said clamp member for locating said outer end of said arm member above and in desired relation with a puncture site on a patient positioned between said arm member and base plate and alongside said support post;
   a pressure pad defining an attachment socket; and
   a pressure adjustment mechanism mounted to said portion of said patient size adjustment mechanism for movement toward and away from the patient, said mechanism having a lower end defining a ball received within said attachment socket and rotatable with respect thereto, said lower end supporting said pressure pad at the puncture site and in pressure contact therewith wherein the amount of the pressure applied to the puncture site by said pad is adjustable upon movement of said pressure adjustment mechanism toward and away the patient.

2. The apparatus of claim 1 in which said pressure pad includes:
   a disc-shaped portion having a peripheral edge and a puncture site contacting side and an opposite side;

a joint element defined centrally on said opposite side of disc-shaped portion and connected with said pressure adjustment mechanism lower end; and a heel portion formed about and along a portion of said peripheral edge of said disc-shaped portion.

3. The apparatus of claim 2 in which said heel portion projects outwardly from and is integrally attached along said portion of said peripheral edge of said disc-shaped portion.

4. The apparatus of claim 2 in which said disc-shaped portion has a groove defined in said puncture site contacting side thereof.

5. The apparatus of claim 4 in which said groove is defined in said puncture site contacting side of said disc-shaped portion so as to extend a central location thereon to said another portion of said peripheral edge thereof.

6. The apparatus of claim 5 in which said groove divergently tapers from said central location to said peripheral edge of said disc-shaped portion, being widest at said portion thereof adjacent said peripheral edge.

7. The apparatus of claim 3 in which said pad defines stiffening ribs extending across the opposite side of said disc-shaped portion adjacent said heel portion so as to stiffen part of said pad.

8. The apparatus of claim 7 in which said disc-shaped portion is relatively flexible in the region not reinforced by said ribs.

9. The apparatus of claim 1 in which said pressure adjustment mechanism includes:

an elongated member mounted to said outer end of said arm member for generally vertical movement relative thereto toward and away from said base plate and the patient positioned between said base plate and said arm member, said elongated member having a lower end defining said ball.

10. Adjustable compress apparatus for use in applying adjustable pressure to a puncture site on a patient, comprising:

an adjustable stand including
a base plate;
a support post attached on said base plate and extending upright therefrom;
a clamp member mounted on said support post above said base plate for slidable movement generally vertically along said support post toward and away from said base plate;
an arm member mounted on said clamp member for slidable movement generally horizontally therealong, in transverse relation to said support post and generally parallel relation to said base plate, said arm member having an outer end overlying and spaced above said base plate; and
a releasable locking member for fastening said clamp member at any selected vertical position along said support post and said arm member at any selected horizontal position along said clamp member for locating said outer end of said arm member above and in desired relation with a puncture site on a patient positioned between said arm member and base plate and alongside said support post;

a pressure pad adapted to make pressure contact with the puncture site on the patient including
a disc-shaped portion having a peripheral edge and a puncture site contacting side and an opposite side, and
a joint element defined centrally on said opposite side of disc-shaped portion; and a pressure adjustment mechanism including
an elongated member mounted to said outer end of said arm member for generally vertical movement relative thereto toward and away from said base plate and the patient positioned between said base plate and said arm member, said elongated member having a lower end disposed adjacent to the puncture site when said outer end of said arm member is located above and in said desired relation with the puncture site; and
another joint element on said lower end of said elongated member for pivotally mating with said joint element of said pressure pad for permitting generally omi-directional movement of said pad relative to the patient for self-adjustment of said pad into conformity with the contour of the puncture site on the patient.

11. The appartus of claim 10 in which said another joint element on said lower end of said elongated member is a ball and said joint element on said pressure pad is a socket which releasably mates with said ball.

12. The apparatus of claim 10 in which said pad further defines a heel portion which projects outwardly and is integrally attached along a portion of the peripheral edge of said disc-shaped portion.

13. An adjustable compress stand for use in applying adjustable pressure to a puncture site on a patient, comprising:

a support frame extending in upright relation and disposable closely adjacent to a patient when reclining on a support surface, said support frame including a base plate and a support post attached to said base plate and extending upright therefrom;
a patient size adjustment mechanism mounted to said support frame for movement along said support frame to adjust said mechanism to a height greater than that of a puncture site on the patent above the support surface and for movement generally transverse to said support frame to adjust said mechanism to a range of distances across the patient from the puncture site thereon to said support frame when disposed closely adjacent to the patient so as to locate a portion of said mechanism in a desired relation overlying the puncture site on the patient, said mechanism including a clamp member mounted on said support post above said base plate for slidable movement generally vertically along said support post toward and away from said base plate;
an arm member mounted on said clamp member for slidable movement generally horizontally therealong, in transverse relation to said support post and generally parallel relation to said base plate, said arm member having an outer end defining said portion of said patient size adjustment mechanism overlying said base plate; and
a releasable locking member for fastening said clamp member at any selected vertical position along said support post and said arm member at any selected horizontal position along said clamp member for locating said outer end of said arm member above and in desired relation with a puncture site on a patient positioned between said arm member and said base plate and alongside said support post; and a pressure adjustment mechanism including a threaded shaft, extending through a threaded opening in said portion of said patient size adjustment mechanism, for movement toward and away from the patient when the patient is reclining on the support surface by rotation of said shaft, said mechanism having a lower end disposed adjacent to the puncture site when said support frame is disposed closely adjacent the side of the patient and said portion of said patient size adjustment mechanism is located in said desired relation overlying the puncture site, said lower end adapted to support means at the puncture site in pressure contact therewith wherein the amount of the pressure is adjustable upon rotation of said shaft so as to effect movement of said pressure adjustment mechanism toward and away the patient.

14. The stand of claim 13 in which said pressure adjustment mechanism includes:

a joint defining said lower end of said threaded shaft, said joint pivotally connecting said pressure applying means to said lower end of said shaft for permitting movement of said pressure applying means relative to the patient for self-adjustment thereof into conformity contour of the with the patient's body.

15. An adjustable compress stand for use in applying variable pressure to a puncture site on a patient, comprising:

a base plate;

a support post attached on said base plate and extending upright therefrom;

a clamp member mounted on said support post above said base plate for slidable movement generally vertically along said support post toward and away from said base plate;

an arm member mounted on said clamp member for slidable movement generally horizontally therealong, in transverse relation to said support post and generally parallel relation to said base plate, said arm member having an outer end overlying and spaced above said base plate;

a releasable locking member for fastening said clamp member at any selected vertical position along said support post and said arm member at any selected horizontal position along said clamp member for locating said outer end of said arm member above and in desired relation with a puncture site on a patient positioned between said arm member and base plate and alongside said support post;

an elongated member mounted to said outer end of said arm member for generally vertical movement relative thereto toward and away from said base plate and the patient positioned between said base plate and said arm member, said elongated member having a lower end disposed adjacent to the puncture site when said outer end of said arm member is located above and in said desired relation with the puncture site; and a joint element on said lower end of said elongated for pivotally connecting a puncture site pressure pad to said elongated member for permitting movement of the pad relative to the patient for self-adjustment of the pad into conformity with the contour of the puncture site on the patient.

16. A pad for use in applying pressure to a puncture site on a patient, comprising:

a disc-shaped portion having a peripheral edge and a puncture site contacting side and an opposite side;

a heel portion formed about and along a portion of said peripheral edge of said disc-shaped portion, but absent from another portion of said peripheral edge thereof, a joint element defined centrally on said opposite side of disc-shaped portion; said joint element defining a cavity which is generally spherical in shape and thereby part of a releasable ball-and-socket arrangement permitting movement of said pad relative to the patient for self-adjustment of said pad into conformity with the contour of the patient's body, and a plurality of stiffening ribs extending from said joint outwardly to said heel portion whereby part of said disc-shaped portion is relatively inflexible.

17. The pad of claim 16 in which said heel portion projects outwardly from and is integrally attached along said portion of said peripheral edge of said disc-shaped portion.

18. The pad of claim 16 in which said puncture site contacting side is textured to reduce slipping between said pad and the skin of the patient.

19. The pad of claim 16 in which said disc-shaped portion is generally transparent.

* * * * *